United States Patent
Matsushima et al.

(10) Patent No.: US 9,134,224 B2
(45) Date of Patent: Sep. 15, 2015

(54) GAS COMPONENT DETECTION DEVICE

(75) Inventors: Shunsuke Matsushima, Osaka (JP); Eiichi Furukubo, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 92 days.

(21) Appl. No.: 14/110,999

(22) PCT Filed: Apr. 5, 2012

(86) PCT No.: PCT/IB2012/000693
§ 371 (c)(1),
(2), (4) Date: Oct. 10, 2013

(87) PCT Pub. No.: WO2012/140485
PCT Pub. Date: Oct. 18, 2012

(65) Prior Publication Data
US 2014/0070101 A1 Mar. 13, 2014

(30) Foreign Application Priority Data
Apr. 11, 2011 (JP) .................. 2011-086891

(51) Int. Cl.
*G01N 21/17* (2006.01)
*G01N 21/3504* (2014.01)

(52) U.S. Cl.
CPC ............ *G01N 21/17* (2013.01); *G01N 21/3504* (2013.01)

(58) Field of Classification Search
CPC ........................... G01N 21/17; G01N 21/3504
See application file for complete search history.

(56) References Cited

U.S. PATENT DOCUMENTS

| | | | |
|---|---|---|---|
| 5,747,808 A * | 5/1998 | Wong | 250/343 |
| 6,067,840 A | 5/2000 | Chelvayohan et al. | |
| 6,396,056 B1 * | 5/2002 | Lord et al. | 250/252.1 |
| 6,410,918 B1 | 6/2002 | Kouznetsov | |
| 2005/0259262 A1 | 11/2005 | Fischer et al. | |
| 2005/0280825 A1 | 12/2005 | Oka et al. | |
| 2005/0285039 A1 | 12/2005 | Ludwig | |
| 2006/0219923 A1 | 10/2006 | Uchida et al. | |

(Continued)

FOREIGN PATENT DOCUMENTS

| | | |
|---|---|---|
| JP | 64-13439 | 1/1989 |
| JP | 09-184803 | 7/1997 |

(Continued)

OTHER PUBLICATIONS

International Search report dated Jun. 12, 2012 with English language translation.

*Primary Examiner* — David Porta
*Assistant Examiner* — Mindy Vu
(74) *Attorney, Agent, or Firm* — Greenblum & Bernstein, P.L.C.

(57) ABSTRACT

An optical path of infrared rays (see the broken lines in FIG. 1) is modified to a substantially U-like shape by a first reflecting mirror and a second reflecting mirror. An incidence angle of the infrared rays incident on the wavelength filter (an angle between the infrared rays incident on the surface of the wavelength filter and the line perpendicular to the surface of the wavelength filter) is nearly zero. For this reason, as compared with a conventional example, the influence of the incidence angle dependence of the wavelength filter can be reduced. As a result, the amount of the infrared rays reaching the light receiving unit through the wavelength filter is increased, thereby suppressing a decline in the detection accuracy of the gas component.

23 Claims, 11 Drawing Sheets

(56) References Cited

U.S. PATENT DOCUMENTS

2008/0316489 A1 12/2008 Ludwig
2009/0039267 A1 2/2009 Arndt et al.

FOREIGN PATENT DOCUMENTS

| JP | 11-118711 | 4/1999 |
| JP | 2001-153801 | 6/2001 |
| JP | 2002-350341 | 12/2002 |
| JP | 2005-233958 | 9/2005 |
| JP | 2006-3233 | 1/2006 |
| JP | 2006-17712 | 1/2006 |
| JP | 2006-514745 | 5/2006 |
| JP | 2006-275980 | 10/2006 |
| JP | 2006-300738 | 11/2006 |
| JP | 2007-507723 | 3/2007 |

* cited by examiner

GAS COMPONENT DETECTION DEVICE

FIELD OF THE INVENTION

The present invention relates to a gas component detection device for detecting a gas component concentration using an absorption property of infrared rays.

BACKGROUND OF THE INVENTION

As the conventional gas component detection devices, there are available an infrared gas detector disclosed in Patent Document 1 and an infrared gas analyzer disclosed in Patent Document 2.

The conventional example disclosed in Patent Document 1 includes a housing into which a detection target gas (e.g., carbon monoxide) is introduced, a light source for irradiating infrared rays into the housing, and an infrared detector for detecting infrared rays existing within the housing. The light source is formed of a package-type light emitting diode which includes a light emitting diode chip (a bare element), a stem to which the bare element is mounted and an encapsulation material for encapsulating the bare element. The light source emits infrared rays as an electric power is supplied thereto from a lead terminal protruding from the stem. The infrared detector is formed of a package-type photo diode which includes a photo diode chip (a bare element), a stem to which the bare element is mounted and an encapsulation material for encapsulating the bare element. A detection signal is produced by a lead terminal protruding from the stem. The infrared detector is provided with a wavelength filter (a wavelength selecting filter) whose passband includes a wavelength region of infrared rays absorbed by a detection target gas. In this conventional example, a space having an ellipsoid shape is formed within the housing. The light emitting diode chip and the photo diode chip are positioned in two focal points of the ellipsoid. The conventional example disclosed in Patent Document 2 includes a box-shaped metal case, an elliptical reflection mirror arranged within the metal case, a light source and an optical receiver arranged to face the reflection surface of the elliptical reflection mirror, and a wavelength filter whose passband includes a wavelength region of infrared rays absorbed by a detection target gas, the wavelength filter provided on the light receiving surface of the optical receiver. A vent hole is formed in the metal case. A gas including a detection target gas (e.g., carbon dioxide) is introduced into the metal case through the vent hole. The concentration of the detection target gas existing within the housing or the metal case can be detected depending on the amount (level) of the infrared rays irradiated from the light source and received by the infrared detector or the optical receiver without being absorbed by the detection target gas.

[Patent Document 1] Japanese Patent Application Publication No. 2006-275980A

[Patent Document 2] Japanese Patent Application Publication No. H9-184803

The wavelength filter used in the conventional examples is usually formed of a band pass filter (an interference filter) including a dielectric multi-layer film. Therefore, the wavelength filter has a drawback in that the incidence angle dependence thereof is high. In other words, in a case of the conventional examples disclosed in Patent Document 1 or Patent document 2, there is a concern that, among the infrared rays having a wavelength belonging to a passband, most of the infrared rays, which are emitted from the light source and reflected by the inner surface of the ellipsoid or the reflection surface of the elliptical reflection mirror, may not pass through the wavelength filter. Further, when the amount of the infrared rays passing through the wavelength filter and reaching the infrared detector or the optical receiver decreases, the detection accuracy of gas components declines.

In view of the problems noted above, it is an object of the present invention to suppress the decrease in the amount of a received infrared ray attributable to the incidence angle dependence of a wavelength filter.

SUMMARY OF THE INVENTION

In accordance with the present invention, there is provided a gas component detection device, including: at least one light emitting unit for emitting infrared rays; at least one light receiving unit for receiving the infrared rays and converting the infrared rays to an electric signal; a holding body for holding the light emitting unit and the light receiving unit; at least one light guide body for guiding an optical path of the infrared rays emitted from the light emitting unit to a light reception surface of the light receiving unit; and at least one wavelength filter whose passband includes a predetermined wavelength region, the wavelength filter arranged in the optical path of the infrared rays guided by the light guide body, wherein the light guide body includes a first reflecting mirror arranged to face the light emitting unit, a second reflecting mirror arranged to face the light reception surface of the light receiving unit and a third reflecting mirror arranged between the first reflecting mirror and the second reflecting mirror.

In the gas component detection device, the light guide body may further include a dividing portion for dividing the optical path of the infrared rays reflected by the first reflecting mirror into a plurality of optical paths, and the second reflecting mirror may be divided and arranged in each of the optical paths divided by the dividing portion.

In the gas component detection device, plural groups of the light emitting unit, the light receiving unit, the wavelength filter and the light guide body may be provided.

In the gas component detection device, the first reflecting mirror may have a parabolic reflection surface, and the light emitting unit may be arranged in a focal point position of the parabolic reflection surface.

In the gas component detection device, the second reflecting mirror may have a curved reflection surface.

In the gas component detection device, the light emitting unit may be formed of a semiconductor chip for emitting the infrared rays, and the light receiving unit may be formed of a semiconductor chip for receiving the infrared rays and converting the infrared rays to the electric signal.

In the gas component detection device, the wavelength filter may include a first wavelength filter whose passband includes a wavelength region absorbed by a detection target gas and a second wavelength filter whose passband does not include the wavelength region absorbed by the detection target gas but includes a wavelength region near the wavelength region absorbed by the detection target gas, and wherein the light receiving unit may include a first light receiving unit for receiving the infrared rays passing through the first wavelength filter and a second light receiving unit for receiving the infrared rays passing through the second wavelength filter.

The gas component detection device may further include a signal processing circuit unit for processing the electric signal outputted from the light receiving unit, and the signal processing circuit unit may be arranged outside the light guide body and between the light emitting unit and the light receiving unit.

In the gas component detection device, a fourth reflecting mirror may be arranged between the signal processing circuit unit and the optical path.

In the gas component detection device, the fourth reflecting mirror having a surface serving as a reflection surface may be formed into a flat plate shape, and may be held by the holding body such that the reflection surface is flush with a light emission surface of the light emitting unit.

In the gas component detection device, a wall for shielding the infrared rays emitted from the light emitting unit may be arranged between the light emitting unit and the signal processing circuit unit.

In the gas component detection device, the wall may be integrally formed with the holding body.

In the gas component detection device, the wavelength filter may be held by the holding body, together with the light receiving unit.

In the gas component detection device, the wavelength filter may be arranged within the light guide body.

In the gas component detection device, a lens for collecting light may be arranged in the optical path between the light emitting unit and the light guide body.

In the gas component detection device, the wavelength filter may be attached to the light receiving unit.

In the gas component detection device, the holding body may be a three-dimensional wiring substrate on which wirings leading to the light emitting unit and the light receiving unit are integrally formed.

The gas component detection device may further include a cover configured to hold the light guide body and coupled to the holding body, wherein the cover may include a projection protruding from a coupling surface of the cover coupled to the holding body, the holding body may include a fitting hole formed on a coupling surface of the holding body coupled to the cover, the projection fitted to the fitting hole, and a hole smaller in diameter than the fitting hole may be formed on a bottom surface of the fitting hole.

Effect of the Invention

The gas component detection device of the present invention has an effect of suppressing the decrease in the amount of a received infrared ray attributable to the incidence angle dependence of a wavelength filter.

BRIEF DESCRIPTION OF THE DRAWINGS

The objects and features of the present invention will become apparent from the following description of embodiments, given in conjunction with the accompanying drawings, in which.

DETAILED DESCRIPTION OF THE EMBODIMENTS

Hereinafter, embodiments of a gas component detection device in accordance with the present invention will now be described in detail with reference to the accompanying drawings. The following embodiments are presented by way of example and the present invention will not be limited to the following embodiments.

First Embodiment

Figure 2:
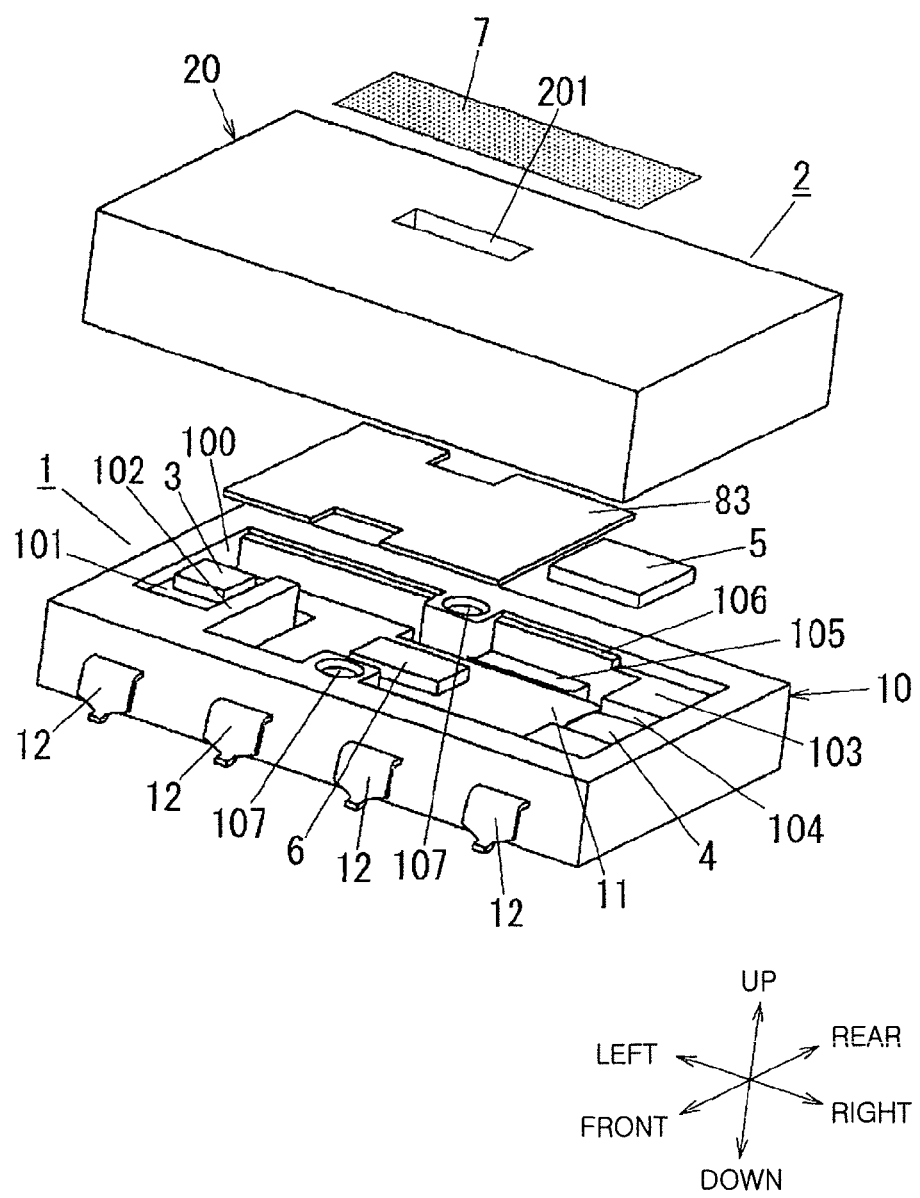
FIG. 2 is a schematic exploded perspective view of the first embodiment.

Referring to FIG. 2, a gas component detection device (hereinafter referred to as a "gas sensor") in accordance with the present embodiment includes a circuit block 1 and an optical block 2. In the following description, up-down, left-right, and front-rear directions will be defined on the basis of FIG. 2.

The circuit block 1 includes a body 10 formed of a synthetic resin molded body and a wiring substrate 11 accommodated within the body 10. A light emitting unit 3, a light receiving unit 4, a wavelength filter 5 and a signal processing circuit unit 6 are mounted on the wiring substrate 11. The light emitting unit 3 is formed of a semiconductor bare chip for emitting infrared rays (e.g., a light emitting diode chip or a light source obtained by forming a resistor element on a semiconductor substrate using a micro electro-mechanical systems (MEMS) technology). The wavelength of the infrared rays emitted from the light emitting unit 3 is susceptible to absorption to a detection target gas (e.g., carbon dioxide, carbon monoxide, methane or nitrogen oxide). The light receiving unit 4 is formed of a semiconductor bare chip (e.g., a photodiode chip or a pyroelectric element) for receiving the infrared rays and converting the infrared rays to an electric signal. The wavelength filter 5 is formed of a band pass filter whose passband includes a predetermined wavelength region, e.g., a wavelength region, which is absorbed by the detection target gas, among the wavelengths of the infrared rays emitted from the light emitting unit 3. The band pass filter of this kind is often called an interference filter and is mainly composed of a multi-layer dielectric film structure. The signal processing circuit unit 6 is formed of an integrated circuit (IC) for driving the light emitting unit 3 to emit infrared rays and for performing signal processing, such as amplifying, waveform shaping, sampling, A/D converting, arithmetic processing, correction processing and abnormal concentration determination processing, with respect to the signal outputted from the light receiving unit 4.

Figure 3:
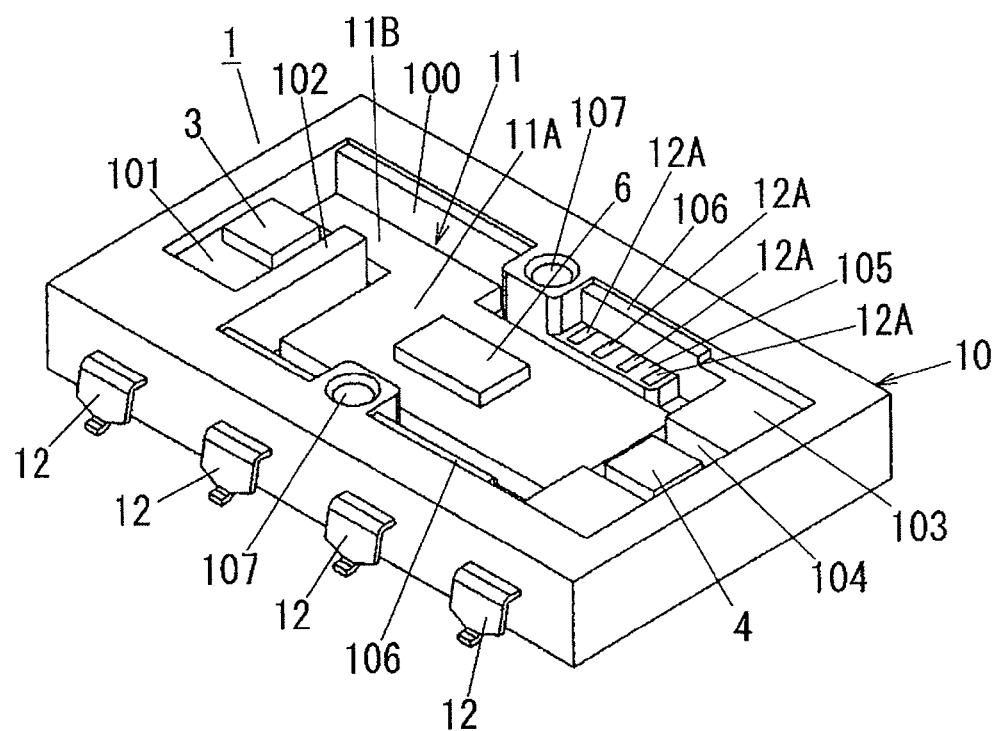
FIG. 3 is a schematic perspective view showing a circuit block of the first embodiment.

As shown in FIG. 3, the wiring substrate 11 includes a rectangular main portion 11A and a rectangular extension portion 11B extending leftward from the left rear end of the main portion 11A, the extension portion 11B being smaller in size than the main portion 11A and being integrally formed with the main portion 11A. The signal processing circuit unit 6 is mounted on the substantially central region of the main portion 11A. Printed wirings (not shown) are formed on the upper surface of the main portion 11A and the upper surface of the extension portion 11B. In other words, the signal processing circuit unit 6 is arranged outside a light guide body 8 and between the light emitting unit 3 and the light receiving unit 4.

The body 10 is formed into a flat rectangular parallelepiped shape and is provided with a recess portion 100 opened on the upper surface of the body 10. The wiring substrate 11 is accommodated within the recess portion 100. A depressed portion 101 is formed in the left end region of the upper surface of the body 10. The light emitting unit 3 is mounted on the bottom surface (lower surface) of the depressed portion 101 (see FIG. 1). In the present embodiment, the body 10 serves as a holding body. The light emitting unit 3 is electrically connected to the printed wirings of the extension portion 11B by a suitable method such as wire bonding or the like. A wall 102 substantially identical in height with the upper surface of the body 10 is installed at the right side of the depressed portion 101. In other words, the wall 102 is installed between the light emitting unit 3 and the signal processing circuit unit 6. The infrared rays emitted from the light emitting unit 3 are shielded by the wall 102, thereby suppressing an erroneous operation of the signal processing circuit unit 6 otherwise caused by the irradiation of the infrared rays. The wall 102 is integrally formed with the body 10. This provides an advantage in that, as compared with a case where the wall 102 is formed independently of the body 10, cost-effectiveness and size reduction can be achieved.

In the right end region of the upper surface of the body 10, there are formed an upper depressed portion 103 having a depth in the up-down direction substantially equal to the thickness (height in the up-down direction) of the wavelength filter 5, and a lower depressed portion 104 positioned at the center in the front-rear direction of the upper depressed portion 103. The light receiving unit 4 is mounted on the bottom surface (lower surface) of the lower depressed portion 104. The wavelength filter 5 is arranged at the center of the upper depressed portion 103 so as to cover the upper side of the light receiving unit 4 (see FIG. 1). The light receiving unit 4 is electrically connected to the printed wirings of the main portion 11A by a suitable method such as wire bonding or the like. In the present embodiment, the light receiving unit 4 and the wavelength filter 5 are held by the body 10. Thus, there is no need to arrange the wavelength filter 5 within a package. This provides an advantage in that cost-effectiveness and size reduction can be achieved.

As shown in FIGS. 2 and 3, a plurality of (four, in the illustrated example) protruding terminals 12 is arranged on both of the front and the rear surface of the body 10 along the left-right direction. The terminals 12 are formed of metal plates and are insert-molded in the body 10. Stand portions 105 having a rectangular column shape are formed in the front and the rear region within the recess portion 100 (the rear stand portion is only illustrated). The end portions of the four terminals 12 protruding from the front surface of the body 10 are exposed on the upper surface of the front stand portion 105. The end portions 12A of the four terminals 12 protruding from the rear surface of the body 10 are exposed on the upper surface of the rear stand portion 105. The end portions 12A of the respective terminals 12 exposed on the stand portions 105 are electrically connected to the printed wirings of the wiring substrate 11 by a suitable method such as wire bonding or the like.

Figure 1:
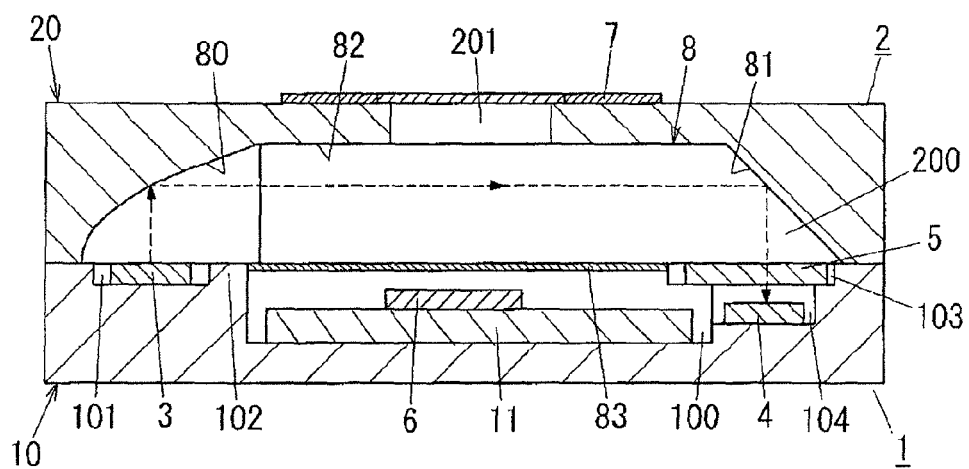
FIG. 1 is a schematic cross-sectional view showing a first embodiment.

The optical block 2 includes a cover 20 formed of a synthetic resin molded body and the light guide body 8 arranged within the cover 20 (see FIG. 1). The cover 20 is formed into a rectangular parallelepiped shape to have front-rear and left-right dimensions equal to those of the body 10. The cover 20 is provided with a recess portion 200 opened on the lower surface thereof. The cover 20 is joined to the upper surface of the body 10 in a state that the light guide body 8 is arranged within the recess portion 200. A rectangular vent hole 201 penetrating through the cover 20 in the up-down direction is formed in the central region of the upper portion of the cover 20. An ambient gas (a mixture of different kinds of gases including a detection target gas) is introduced into the recess portion 200 (the light guide body 8) through the vent hole 201. The shape of the vent hole 201 is not limited to the rectangular shape but may be a circular shape or other shapes. Moreover, there may be provided a plurality of vent holes. In order to prevent foreign materials other than an ambient air, e.g., dust, from infiltrating through the vent hole 201, the opening of the vent hole 201 existing on the upper surface of the cover 20 is covered with a dustproof filter 7 (see FIG. 1).

As shown in FIG. 1, the light guide body 8 includes a first reflecting mirror 80, a second reflecting mirror 81, a third reflecting mirror 82 and a fourth reflecting mirror 83. The first reflecting mirror 80 has a reflection surface of, e.g., a parabolic shape, and serves to reflect (change) the optical path (optical axis) (see a broken line in FIG. 1) of the infrared rays emitted from the light emitting unit 3 to the direction (the left-right direction) along the upper surface of the body 10. The second reflecting mirror 81 has a reflection surface of, e.g., a flat shape, and serves to reflect (change) the optical path (optical axis) changed by the first reflecting mirror 80 to the direction (the up-down direction) intersecting with the light receiving surface (upper surface) of the light receiving unit 4. The wavelength filter 5 is arranged in the optical path of the infrared rays guided by the light guide body 8. In the present embodiment, the wavelength filter 5 is arranged between the second reflecting mirror 81 and the light receiving unit 4. The third reflecting mirror 82 is arranged between the first reflecting mirror 80 and the second reflecting mirror 81 and is formed into a semi-cylindrical shape. A hole (not shown) connected to the vent hole 201 of the cover 20 is formed in the central region of the third reflecting mirror 82. The first, the second and the third reflecting mirror 80, 81 and 82 may be made of a metallic material and may be insert-molded in the cover 20. Alternatively, the reflecting mirrors 80, 81 and 82 may be formed by depositing or plating metal such as aluminum or the like on the inner surface of the recess portion 200. In particular, if the reflecting mirrors 80, 81 and 82 are formed by—depositing or plating, it is possible to achieve cost-effectiveness and improved accuracy as compared with a case where the reflecting mirrors 80, 81 and 82 are made of a metallic material.

As shown in FIG. 2, the fourth reflecting mirror 83 is formed into the shape of a flat plate made of a metallic material such as aluminum or the like. Alternatively, the fourth reflecting mirror 83 may be formed into the shape of a flat plate by depositing or plating metal such as aluminum or the like on a molding. Steps 106 having a depth substantially equal to the thickness (in the up-down direction) of the fourth reflecting mirror 83 are formed in the front and the rear edge of the recess portion 100 of the body 10. The front and the rear end portion of the fourth reflecting mirror 83 are placed on the steps 106 in a state that the reflection surface of the fourth reflecting mirror 83 faces upward. In other words, as shown in FIG. 1, the opening of the recess portion 100 is closed by the fourth reflecting mirror 83 over a range from the wall 102 of the body 10 to the upper depressed portion 103. That is to say, the fourth reflecting mirror 83 is arranged between the signal processing circuit unit 6 and the optical path.

At this time, if the reflection surface (upper surface) of the fourth reflecting mirror 83 is lower than the light emission surface (upper surface) of the light emitting unit 3, it is necessary to increase the depth of the recess portion 100 for accommodating the signal processing circuit unit 6 and the wiring substrate 11. Thus, the thickness (height) of the body 10 is increased. On the other hand, if the reflection surface of the fourth reflecting mirror 83 is higher than the light emission surface of the light emitting unit 3, the infrared rays are reflected in the end portion of the fourth reflecting mirror 83, as a result of which the loss of the infrared rays is increased. For that reason, there is a need to increase the size of the light emitting unit 3 and the light receiving unit 4. This makes it difficult to reduce the size of the device. In the present embodiment, the fourth reflecting mirror 83 is paced on the steps 106 having a depth substantially equal to the thickness of the fourth reflecting mirror 83, so that the reflection surface of the fourth reflecting mirror 83 is flush with the light emission surface (upper surface) of the light emitting unit 3. Therefore, the aforementioned problems can be avoided.

In the gas sensor configured as described above, the ambient air is introduced into the light guide body 8 through the vent hole 201. The infrared rays emitted from the light emitting unit 3 are absorbed by the detection target gas contained in the ambient air, whereby the amount of the infrared rays received by the light receiving unit 4 becomes smaller. The output signal of the light receiving unit 4 generated depending on the reception amount of the infrared rays is processed by the signal processing circuit unit 6. Accordingly, it is possible to detect the concentration of the detection target gas (gas component) contained in the ambient air existing inside the light guide body 8. The details of the signal processing performed in the signal processing circuit unit 6 for the detection of the gas concentration are well-known in the art and, therefore, will not be described herein.

In the present embodiment, the optical path (see a broken line in FIG. 1) of the infrared rays is converted into a substantially U-like shape by the first reflecting mirror 80 and the second reflecting mirror 81. The incidence angle of the infrared rays incident on the wavelength filter 5 (an angle between the infrared rays incident on the surface of the wavelength filter 5 and the line perpendicular to the surface of the wavelength filter 5) is nearly zero. For this reason, as compared with the conventional example, the influence of the incidence angle dependence of the wavelength filter 5 can be reduced. As a result, the amount of the infrared rays reaching the light receiving unit 4 through the wavelength filter 5 is increased, thereby suppressing a decline in the detection accuracy of the gas component. Further, in the present embodiment, it is possible to reduce a height in the up-down direction (to realize a low profile) without having to shorten the optical path length, as compared with the conventional example disclosed in Patent Document 2 in which the optical path has a substantially V-like shape. The realization of the low profile shortens the distance from the vent hole 201 to the optical path as compared with the conventional example disclosed in Patent Document 2. Therefore, there is provided an advantage of increasing the detection responsiveness to the change in the ratio of the detection target gas in the ambient air. Since the light emitting unit 3 and the light receiving unit 4 are respectively formed of semiconductor bare chips (a light emitting diode chip and a photodiode chip), it is possible to simplify the wirings as compared with the conventional example employing a package-type light emitting diode or a package-type photodiode.

In the present embodiment, the signal processing circuit unit 6 is arranged between the light emitting unit 3 and the light receiving unit 4 and also in a position not overlapping with the optical path changed by the first reflecting mirror 80; namely arranged within the body 10 (within the recess portion 100). This makes it possible to effectively use the dead space, thereby reducing the size of the body 10 and the cover 20.

Figure 4:
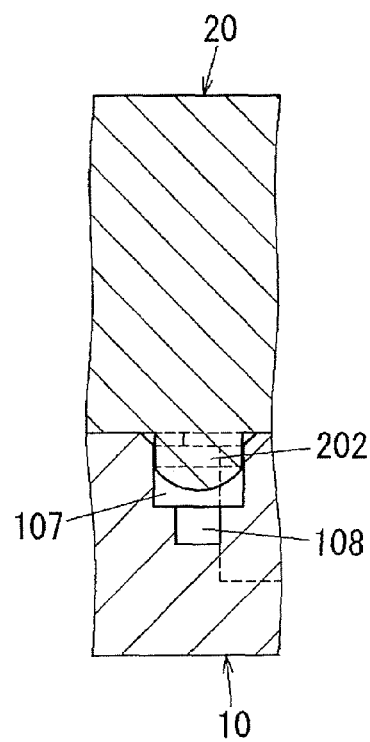
FIG. 4 is a schematic cross-sectional view of major portions of the first embodiment.

Substantially columnar projections 202 are installed at the opposite ends in the front-rear direction of the central region in the left-right direction of the lower surface of the cover 20 so as to protrude downward (see FIG. 4). Circular fitting holes 107 engaging with the projections 202 of the cover 20 are formed at the opposite ends in the front-rear direction of the central region in the left-right direction of the upper surface of the body 10 (see FIGS. 2 and 3). By fitting the projections 202 and the fitting holes 107 together, it is possible to position the body 10 and the cover 20 during the joining process thereof and to easily perform the positioning of the light emitting unit 3 and the first reflecting mirror 80 and the positioning of the light receiving unit 4 and the second reflecting mirror 81. Particularly, in the present embodiment, the reflection surface of the first reflecting mirror 80 is formed into a parabolic surface shape. By positioning the body 10 and the cover 20, the light emitting unit 3 can be easily arranged in the focal point position of the reflection surface (the parabolic surface).

In a case where the gas sensor of the present embodiment is assembled by an automatic assembling machine, the mounting positions of the light emitting unit 3 and the light receiving unit 4 are determined by a well-known image processing technology (e.g., an edge detecting technology) using an image of the body 10 taken by a camera from above. In the present embodiment, as shown in FIG. 4, a hole 108 smaller in diameter than the fitting holes 107 is formed on the bottom surface of each of the fitting holes 107 of the body 10. The position of each of the fitting holes 107 is detected using the edge of the hole 108. The mounting positions of the light emitting unit 3 and the light receiving unit 4 are determined on the basis of the position of each of the fitting holes 107. In a case where the position of each of the fitting holes 107 is detected by a well-known image processing technology based on the edge of each of the fitting holes 107, a position detection error is generated due to the difference in the imaging (focus) position in the taken image. This is because a position in the depth direction of the surface of the light emitting unit 3 or the light receiving unit 4 differs from a position in the depth direction of each of the fitting holes 107. In order to reduce the position detection error, the hole 108 having a small diameter is formed in such a way that a position in the depth direction of the edge of the hole 108 becomes identical or substantially identical with a position in the depth direction of the surface of the light emitting unit 3 or the light receiving unit 4.

In the present embodiment, the determination of the positions of the circuit block 1 and the optical block 2 and the determination of the mounting positions of the light emitting unit 3 and the light receiving unit 4 with respect to the body 10 are performed on the basis of the same fitting holes 107. As a result, there is provided an advantage in that the accuracy of positioning of the light emitting unit 3, the light receiving unit 4 and the light guide body 8 (the first reflecting mirror 80 and the second reflecting mirror 81) becomes higher as compared with a case where the determinations are performed on the basis of different portions from each other. Unlike the illustrated example, it may be possible to employ a single projection 202 and a single fitting hole 107.

Figure 5:
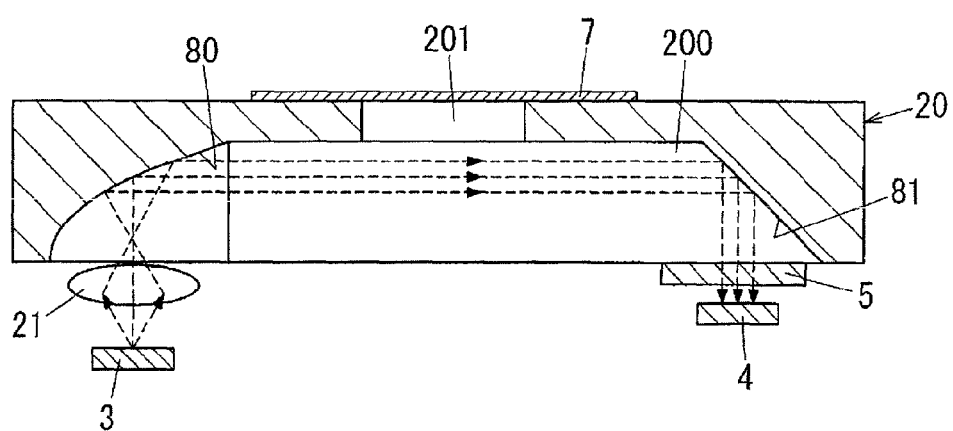
FIG. 5 is a partially cutaway schematic cross-sectional view showing another configuration of the first embodiment.

Since the light emitting unit 3 is not so small as to be regarded as a point light source as compared with the size of the first reflecting mirror 80, only a small fraction of the infrared rays emitted from the light emitting unit 3 passes through the focal point of the reflection surface (parabolic surface) of the first reflecting mirror 80. The partial infrared rays that have not passed through the focal point of the reflection surface are deviated from the incidence angle range of the wavelength filter 5. Thus, the amount of the infrared rays received by the light receiving unit 4 is decreased. For that reason, as shown in FIG. 5, it is preferable to arrange a lens 21 for collecting light on the optical path between the light emitting unit 3 and the first reflecting mirror 80 and to set a light collecting point of the lens 21 to coincide with the focal point of the first reflecting mirror 80. This makes sure that most of the infrared rays emitted from the light emitting unit 3 pass through the focal point of the first reflecting mirror 80. Accordingly, the light receiving unit 4 can efficiently receive the infrared rays.

Figure 6A:
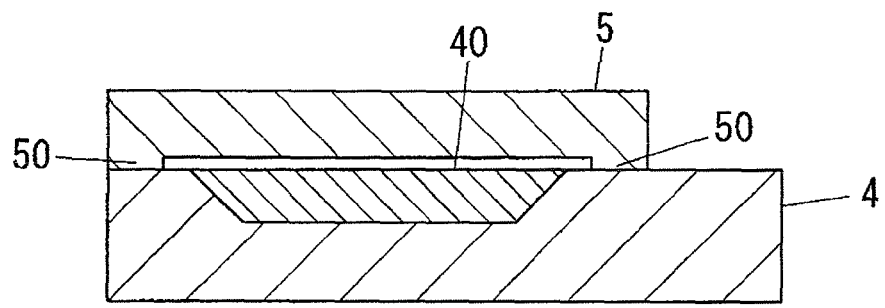
FIG. 6A is a schematic cross-sectional view showing another configuration of a light receiving unit and a wavelength filter of the first embodiment.
Figure 6B:
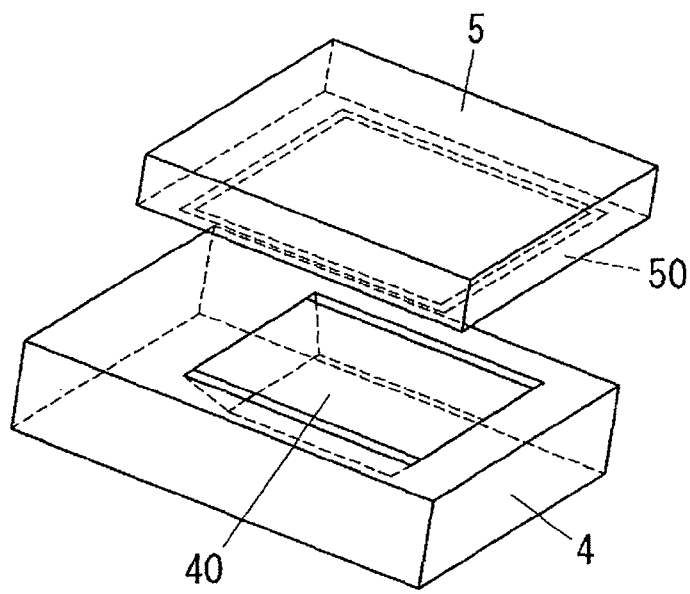
FIG. 6B is a schematic exploded perspective view thereof.
Figure 6C:
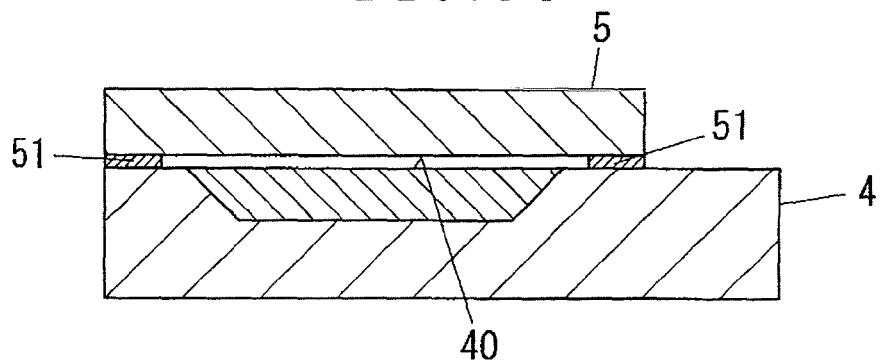
FIG. 6C is a schematic cross-sectional view showing still another configuration of the light receiving unit and the wavelength filter of the first embodiment.

In the present embodiment, the wavelength filter 5 is attached to the body 10. However, as shown in FIGS. 6A to 6C, the wavelength filter 5 may be attached to the light receiving unit 4 (the semiconductor bare chip). For example, a rectangular flat wavelength filter 5 is joined to the upper surface of the light receiving unit 4 so as to cover the light reception surface 40 of the light receiving unit 4. A rim portion 50 is formed in the peripheral edge of the lower surface of the wavelength filter 5. Due to the existence of the rim portion 50, a gap is formed between the light reception surface 40 of the light receiving unit 4 and the lower surface of the wavelength filter 5. Alternatively, a wavelength filter 5 having a planar lower surface may be joined to the light receiving unit 4 by a joining material 51 such as low-melting-point glass, low-melting-point metal or polymer (see FIG. 6C). If the wavelength filter 5 is integrally formed with the light receiving unit 4 in this manner, there is no need to form the upper depressed portion 103 for use in attaching the wavelength filter 5. Moreover, the gap between the wavelength filter 5 and the light reception surface of the light receiving unit 4 becomes smaller. Accordingly, there is provided an advantage in that the thickness of the body 10 can be reduced, thereby achieving a size reduction (realizing a low profile) of the device. In addition, a plurality of light receiving units 4 and a plurality of wavelength filters 5 can be simultaneously manufactured through a semiconductor wafer manufacturing process, and thus the manufacturing cost can be reduced. Alternatively, the wavelength filter 5 may be arranged between the first reflecting mirror 80 and the second reflecting mirror 81, namely within the light guide body.

The reflection surface of the first reflecting mirror 80 is not limited to the parabolic shape, and may have, e.g., a spherical shape or a polygonal shape. Similarly, the reflection surface of the second reflecting mirror 81 is not limited to the planar surface, and may have a curved shape.

Second Embodiment

Figure 7:
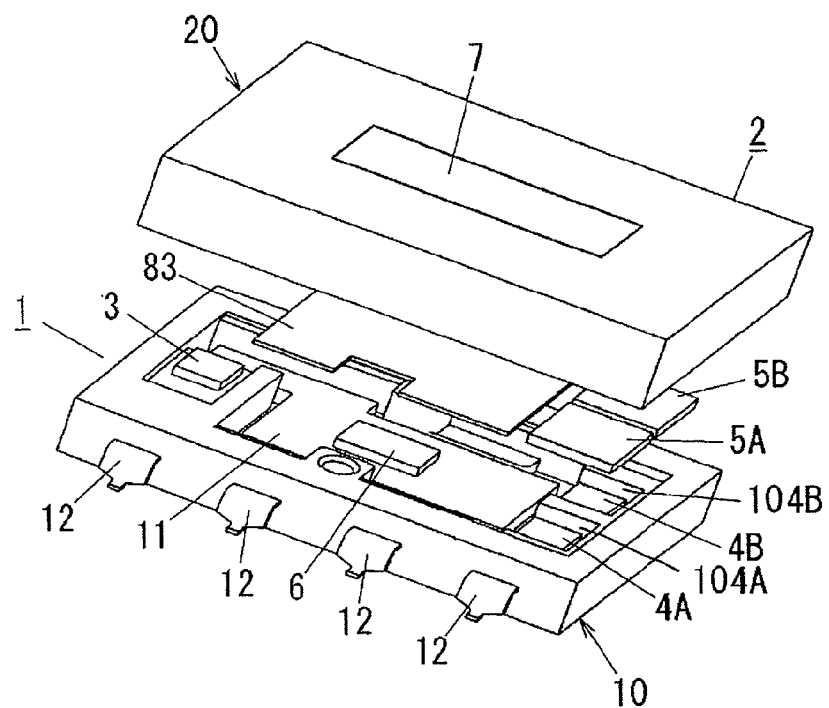
FIG. 7 is a schematic exploded perspective view showing a second embodiment.
Figure 7:
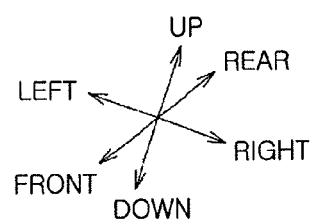

A gas sensor in accordance with the present embodiment is shown in FIG. 7. The gas sensor of the present embodiment is characterized by including two groups of the light receiving unit 4 and the wavelength filter 5. Other configurations remain the same as those of the first embodiment. Therefore, the same components as those of the first embodiment will be designated by like reference symbols, and redundant illustrations and descriptions thereof will be omitted.

As shown in FIG. 7, two lower depressed portions 104A and 104B are formed along the front-rear direction in the right end region of the upper surface of the body 10. A first light receiving unit 4A and a second light receiving unit 4B are mounted on the bottom surfaces of the lower depressed portions 104A and 104B, respectively. A first wavelength filter 5A and a second wavelength filter 5B are arranged on the bottom surface of the upper depressed portion 103 so as to cover the upper surfaces of the light receiving units 4A and 4B, respectively.

In this regard, the first wavelength filter 5A has a passband including a wavelength region of infrared rays absorbed by a detection target gas. However, the second wavelength filter 5B has a passband that does not include the wavelength region of the infrared rays absorbed by the detection target gas but includes, e.g., a wavelength region near the corresponding wavelength region of the infrared rays. In other words, among the infrared rays emitted from the light emitting unit 3, the amount of the infrared rays passing through the first wavelength filter 5A and received by the first light receiving unit 4A is decreased depending on the concentration of the detection target gas, whereas the amount of the infrared rays passing through the second wavelength filter 5B and received by the second light receiving unit 4B is not decreased depending on the concentration of the detection target gas. The signal processing circuit unit 6 obtains a difference between the output signal levels of the first light receiving unit 4A and the second light receiving unit 4B and calculates the concentration of the detection target gas based on the difference.

In a case where, as in the first embodiment, the signal processing circuit unit 6 calculates the gas concentration based on the output signal level of the light receiving unit 4, the detection accuracy of the gas concentration is likely to decline when the output signal level of the light receiving unit 4 is changed by a disturbance factor. On the other hand, if the signal processing circuit unit 6 calculates the concentration of the detection target gas based on the difference between the output signal levels of the first light receiving unit 4A and the second light receiving unit 4B as mentioned above, the variations of the output signal levels of the respective light receiving units 4A and 4B are canceled, thereby suppressing a decline in the detection accuracy of the gas concentration.

Figure 8:
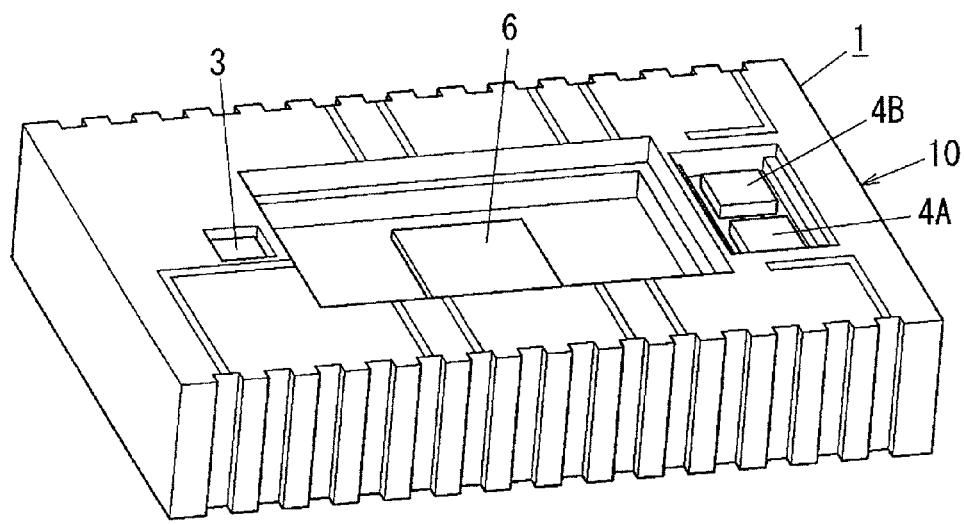
FIG. 8 is a schematic perspective view of a circuit block showing another configuration of the second embodiment.

As shown in FIG. 8, if the body 10 is formed of a three-dimensional wiring substrate (a so-called molded interconnection device (MID) substrate) capable of unifying the wirings leading to the light emitting unit and the light receiving unit, the signal processing circuit unit 6 can be directly mounted on the body 10 without going through the wiring substrate 11. Therefore, the size of the body 10 can be further reduced.

Third Embodiment

Figure 9A:
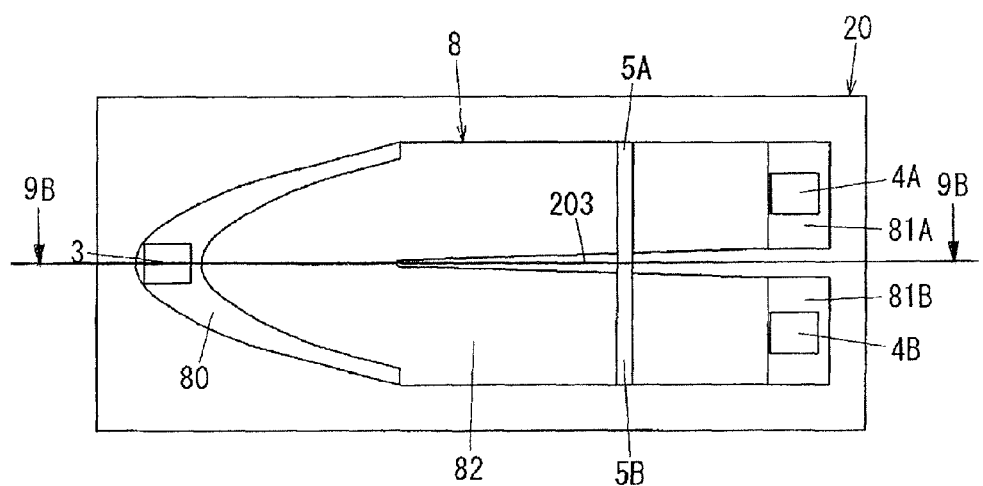
FIG. 9A is a schematic bottom view showing an optical block of a third embodiment.
Figure 9B:
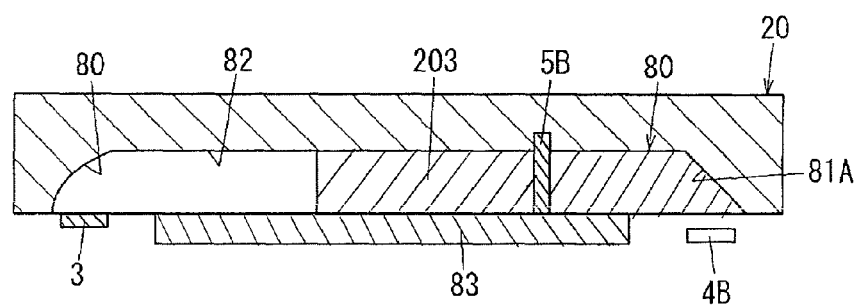
FIG. 9B is a schematic cross-sectional view taken along a line 9B-9B in FIG. 9A.

A gas sensor according to the present embodiment is shown in FIGS. 9A and 9B. The gas sensor of the present embodiment is characterized in the configuration of the optical block 2. Other configurations remain the same as those of the second embodiment. Therefore, the same components as those of the second embodiment will be designated by like reference symbols and redundant illustrations and descriptions thereof will be omitted.

In the present embodiment, as shown in FIG. 9B, the light guide body 8 includes a dividing portion 203 protruding downward from the bottom surface of the recess portion 200 of the cover 20. The dividing portion 203 is formed of a wedge-shaped wall tapering toward the leading end (left end). The rear end (right end) of the dividing portion 203 is positioned between the first light receiving unit 4A and the second light receiving unit 4B to divide the optical path of the infrared rays reflected by the first reflecting mirror 80 into two optical paths (see FIG. 9A). A first wavelength filter 5A and a second wavelength filter 5B are arranged in the optical paths divided by the dividing portion 203, respectively. Second reflecting mirrors 81A and 81B are divisionally arranged in the optical paths, respectively. Thus, the infrared rays traveling along one of the optical paths (a primary optical path) passes through the first wavelength filter 5A, and are reflected by the second reflecting mirror 81A and received by the first light receiving unit 4A. The infrared rays traveling along the other of the optical paths (an auxiliary optical path) pass through the second wavelength filter 5B, and are reflected by the second reflecting mirror 81B and received by the second light receiving unit 4B.

In the second embodiment, the optical path within the light guide body 8 is not divided. Therefore, the incidence range of the infrared rays (hereinafter referred to as a "spot") on the light reception surfaces of the first light receiving unit 4A and the second light receiving unit 4B is relatively large, so that there is a concern that the amount of the infrared rays received in the first light receiving unit 4A and the second light receiving unit 4B may be reduced. In contrast, the optical path within the light guide body 8 is divided in the present embodiment. Therefore, the spot on the light reception surfaces of the first light receiving unit 4A and the second light receiving unit 4B is relatively small. As a result, it is possible to suppress a decrease in the amount of the infrared rays received in the first light receiving unit 4A and the second light receiving unit 4B.

Figure 10A:
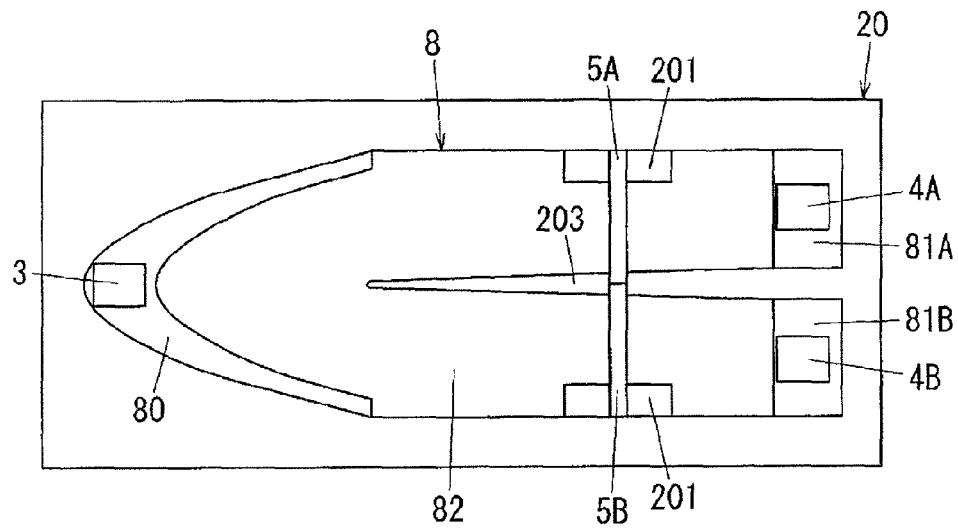
FIGS. 10A and 10B are schematic bottom views showing other configurations of the optical block of the third embodiment.
Figure 10B:
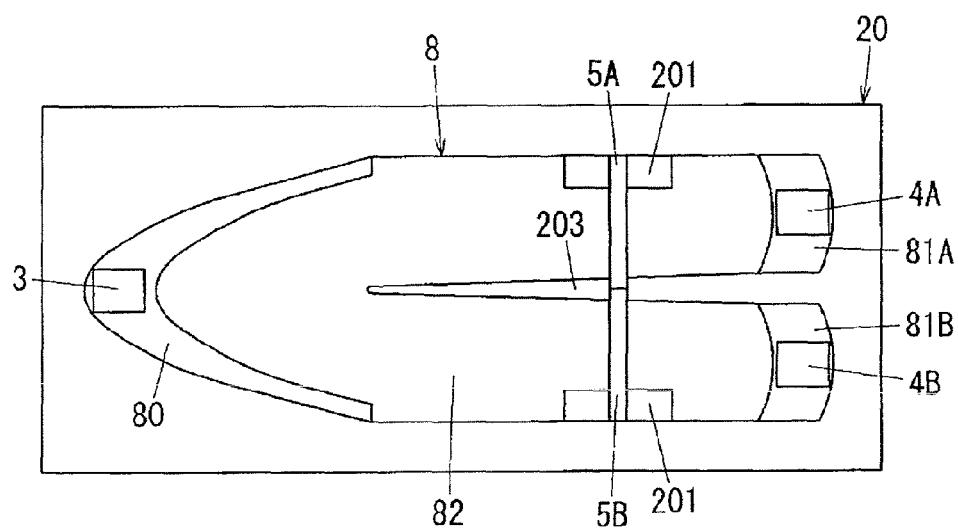

One or more vent holes 201 are formed within the light guide body 8 (see FIGS. 10A and 10B). In a case where the wavelength filters 5A and 5B are installed in the optical paths between the first reflecting mirror 80 and the second reflecting mirrors 81A and 81B, it is preferred that the vent holes 201 are formed between the wavelength filters 5A and 5B and the first reflecting mirror 80, between the wavelength filters 5A and 5B and the second reflecting mirrors 81A and 81B, or across the wavelength filters 5A and 5B. This makes it possible to increase the length of the optical paths over which the infrared rays are absorbed by the detection target gas, thereby enhancing the gas detection accuracy. An optical simulation reveals that a reduced amount of the infrared rays passes through the end regions of the optical paths near the dividing portion 203. Therefore, it is preferred that, as shown in FIGS. 10A and 10B, the vent holes 201 are formed in the opposite end regions of the optical paths from the dividing portion 203.

Figure 11A:
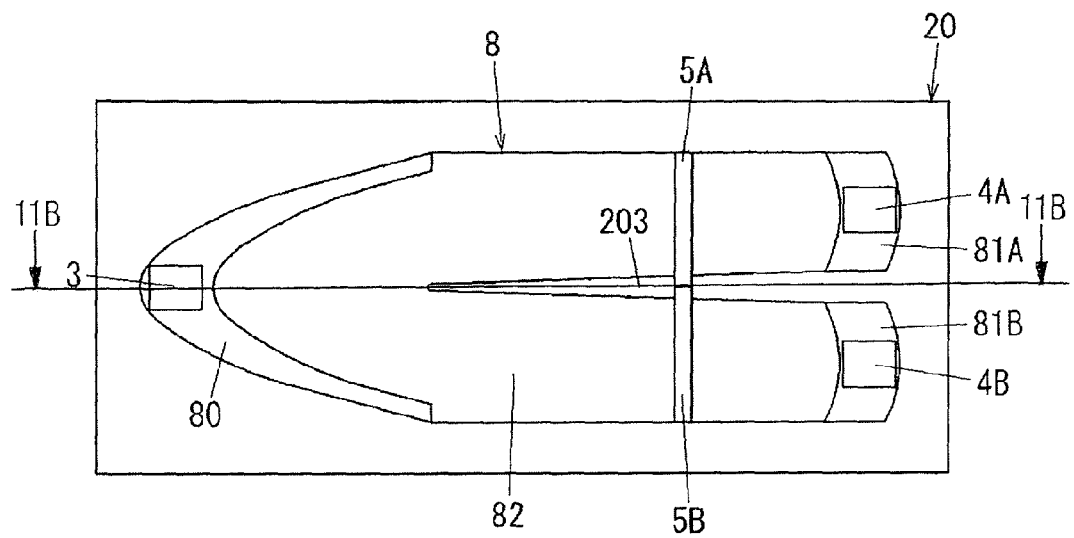
FIG. 11A is a schematic bottom view showing still another configuration of the optical block of the third embodiment.
Figure 11B:
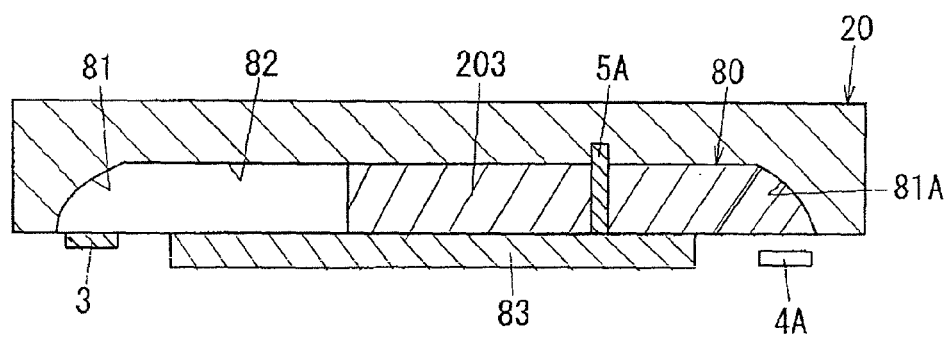
FIG. 11B is a schematic cross-sectional view taken along a line 11B-11B in FIG. 11A.

In this regard, if the reflection surfaces of the second reflecting mirrors 81A and 81B are formed into a curved shape (a concave shape) as shown in FIGS. 11A and 11B, the light reflected by the reflection surfaces of the second reflecting mirrors 81A and 81B is collected to reduce the size of the spot. Therefore, a decrease in the amount of the infrared rays received in the first light receiving unit 4A and the second light receiving unit 4B can be further suppressed.

Fourth Embodiment

Figure 12A:
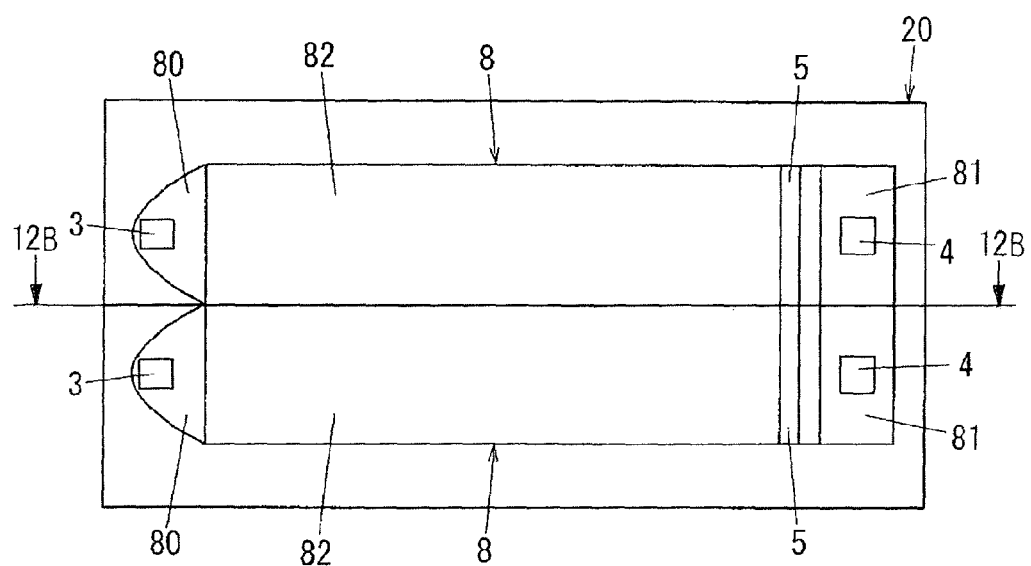
FIG. 12A is a schematic bottom view showing an optical block of a fourth embodiment.
Figure 12B:
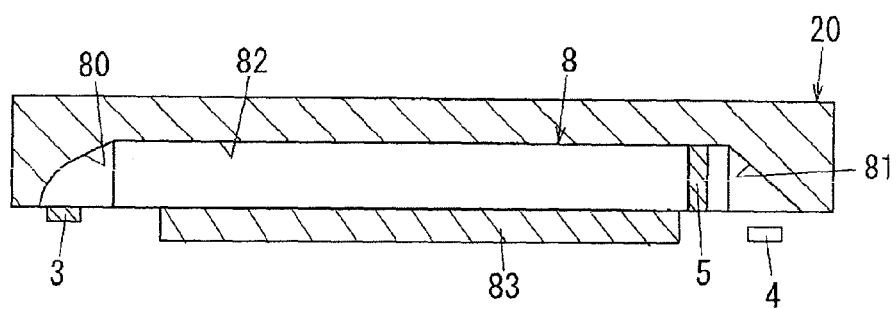
FIG. 12B is a schematic cross-sectional view taken along a line 12B-12B in FIG. 12A.

In the first, second and third embodiments, there are illustrated the gas sensors for detecting the concentration of one kind of gas contained in the ambient air. In contrast, the gas sensor of the present embodiment includes, as shown in FIGS. 12A and 12B, plural groups (two groups, in the illustrated example) of the light emitting unit 3, the light receiving unit 4, the wavelength filter 5 and the light guide body 8. The respective groups are capable of detecting the concentrations of different kinds of gases.

As shown in FIG. 12A, two light emitting units 3 and two light receiving units 4 are mounted on the body. Two light guide bodies 8 for guiding the infrared rays emitted from the respective light emitting units 3 to the respective light receiving units 4 are installed side by side in the recess portion 200 of the cover 20. The configurations of the two light guide bodies 8 are the same as the configuration of the light guide body 8 of the first embodiment except that the wavelength filters 5 are arranged in the optical paths between the first reflecting mirrors 80 and the second reflecting mirror 81. Each of the wavelength filters 5 is formed of a band pass filter whose passband includes the wavelengths corresponding to the absorption properties of the respective detection target gases.

The gas sensor of the present embodiment is capable of independently detecting the concentrations of two different kinds of gases (e.g., carbon monoxide and nitrogen oxide) among the plural kinds of gases contained in the ambient air. In the present embodiment, just like the third embodiment, the reflection surfaces of the second reflecting mirrors 81 may be formed into a curved shape (a concave shape). Further, just like the third embodiment, each group may include a dividing portion, a first light receiving unit 4A, a second light receiving unit 4B, a first wavelength filter 5A and a second wavelength filter 5B, and may detect the concentrations of respective gases from the difference between the output signal levels of the first light receiving unit 4A and the second light receiving unit 4B. Alternatively, a first group may include the first light receiving unit 4A, the second light receiving unit 4B, the first wavelength filter 5A and the second wavelength filter 5B, and a second group may include a single light receiving unit 4 and a single wavelength filter 5. In this case, the first group detects the concentrations of respective gases from the difference between the output signal levels of the first light receiving unit 4A and the second light receiving unit 4B, and the second group detects the concentrations of respective gases from the difference between the output signal levels of the second light receiving unit 4B of the first group and the light receiving unit 4. For the sake of convenience in description, the fourth reflecting mirror 83 is not shown in FIGS. 9A, 10A, 10B, 11A, 11B and 12A. The light emitting unit 3 and the light receiving unit 4 are shown in FIGS. 9A, 9B, 10A, 10B, 11A, 11B, 12A and 12B.

The respective embodiments described above may be combined with one another. While preferred embodiments of the present invention have been described above, the present invention is not limited to these specific embodiments but can be changed and modified in many different forms without departing from the scope of the claims. Such changes and modifications shall be construed to fall within the scope of the present invention.

What is claimed is:
1. A gas component detection device, comprising:
at least one light emitting unit for emitting infrared rays;
at least one light receiving unit for receiving the infrared rays and converting the infrared rays to an electric signal;
a holding body for holding the light emitting unit and the light receiving unit;
at least one light guide body for guiding an optical path of the infrared rays emitted from the light emitting unit to a light reception surface of the light receiving unit; and at least one wavelength filter whose passband includes a predetermined wavelength region, the wavelength filter arranged in the optical path of the infrared rays guided by the light guide body, wherein the light guide body includes a first reflecting mirror arranged to face the light emitting unit, a second reflecting mirror arranged to face the light reception surface of the light receiving unit and a third reflecting mirror arranged between the first reflecting mirror and the second reflecting mirror, and wherein the holding body includes a recess portion arranged between the light emitting unit and the light receiving unit, a bottom surface of the recess portion is arranged below the light emitting unit in a depth direction of the recess portion and the recess portion accommodates a signal processing circuit unit for processing the electric signal outputted from the light receiving unit.

2. The device of claim 1, wherein the first reflecting mirror has a parabolic reflection surface, and the light emitting unit is arranged in a focal point position of the parabolic reflection surface.

3. The device of claim 1,
wherein the signal processing circuit unit is arranged outside the light guide body.

4. The device of claim 3, wherein a fourth reflecting mirror is arranged between the signal processing circuit unit and the optical path.

5. The device of claim 4, wherein a recess portion is provided within the holding body, a step having a depth equal to a thickness of the fourth reflecting mirror is formed in an edge of the recess portion of the body, and the fourth reflecting mirror is mounted on the step.

6. The device of claim 1, wherein a wall for shielding the infrared rays emitted from the light emitting unit is arranged between the light emitting unit and the signal processing circuit unit.

7. The device of claim 1, further comprising:
a cover configured to hold the light guide body and coupled to the holding body, and
wherein the cover includes at least one projection protruding from a coupling surface of the cover coupled to the holding body, the holding body includes a fitting hole formed on a coupling surface of the holding body coupled to the cover, the projection fitted to the fitting hole, and a hole smaller in diameter than the fitting hole is formed on a bottom surface of the fitting hole.

8. The device of claim 1, wherein the wavelength filter is installed in an optical path between the first reflecting mirror and the second reflecting mirror, one or more vent holes are provided in the light guide body.

9. The device of claim 8, wherein the vent holes are arranged between the wavelength filter and the first reflecting mirror.

10. The device of claim 8, wherein the vent holes are arranged between the wavelength filter and the second reflecting mirror.

11. The device of claim 8, wherein the vent holes are arranged on both sides of the wavelength filter.

12. A gas component detection device, comprising:
at least one light emitting unit for emitting infrared rays;
at least one light receiving unit for receiving the infrared rays and converting the infrared rays to an electric signal;
a holding body for holding the light emitting unit and the light receiving unit;
at least one light guide body for guiding an optical path of the infrared rays emitted from the light emitting unit to a light reception surface of the light receiving unit; and
at least one wavelength filter whose passband includes a predetermined wavelength region, the wavelength filter arranged in the optical path of the infrared rays guided by the light guide body, wherein the light guide body includes a first reflecting mirror arranged to face the light emitting unit, a second reflecting mirror arranged to face the light reception surface of the light receiving unit and a third reflecting mirror arranged between the first reflecting mirror and the second reflecting mirror, wherein the gas component detection device further includes a cover configured to hold the light guide body and coupled to the holding body, and wherein the cover includes at least one projection protruding from a coupling surface of the cover coupled to the holding body, the holding body includes a fitting hole formed on a coupling surface of the holding body coupled to the cover, the projection fitted to the fitting hole, and a hole smaller in diameter than the fitting hole is formed on a bottom surface of the fitting hole.

13. The device of claim 12, wherein the first reflecting mirror has a parabolic reflection surface, and the light emitting unit is arranged in a focal point position of the parabolic reflection surface.

14. The device of claim 12, further comprising:
a signal processing circuit unit for processing the electric signal outputted from the light receiving unit, the signal processing circuit unit arranged outside the light guide body and between the light emitting unit and the light receiving unit.

15. The device of claim 14, wherein a fourth reflecting mirror is arranged between the signal processing circuit unit and the optical path.

16. The device of claim 12, wherein a wall for shielding the infrared rays emitted from the light emitting unit is arranged between the light emitting unit and the signal processing circuit unit.

17. The device of claim 12, wherein the wavelength filter is installed in an optical path between the first reflecting mirror and the second reflecting mirror, one or more vent holes are provided in the light guide body.

18. The device of claim 17, wherein the vent holes are arranged between the wavelength filter and the first reflecting mirror.

19. The device of claim 17, wherein the vent holes are arranged between the wavelength filter and the second reflecting mirror.

20. The device of claim 17, wherein the vent holes are arranged on both sides of the wavelength filter.

21. A gas component detection device, comprising:
at least one light emitting unit for emitting infrared rays;
at least one light receiving unit for receiving the infrared rays and converting the infrared rays to an electric signal;
a holding body for holding the light emitting unit and the light receiving unit;
at least one light guide body for guiding an optical path of the infrared rays emitted from the light emitting unit to a light reception surface of the light receiving unit;
at least one wavelength filter whose passband includes a predetermined wavelength region, the wavelength filter arranged in the optical path of the infrared rays guided by the light guide body; and a signal processing circuit unit for processing the electric signal outputted from the light receiving unit, wherein the light guide body includes a first reflecting mirror arranged to face the light emitting unit, a second reflecting mirror arranged to face the light reception surface of the light receiving unit and a third reflecting mirror arranged between the first reflecting mirror and the second reflecting mirror, wherein the signal processing circuit unit is arranged outside the light guide body and between the light emitting unit and the light receiving unit, wherein a fourth reflecting mirror is arranged between the signal processing circuit unit and the optical path, and wherein a recess portion is provided within the holding body, a step having a depth equal to a thickness of the fourth reflecting mirror is formed in an edge of the recess portion of the body, and the fourth reflecting mirror is mounted on the step.

22. The device of claim 21, wherein the first reflecting mirror has a parabolic reflection surface, and the light emitting unit is arranged in a focal point position of the parabolic reflection surface.

23. The device of claim 21, further comprising:

a cover configured to hold the light guide body and coupled to the holding body, and wherein the cover includes at least one projection protruding from a coupling surface of the cover coupled to the holding body, the holding body includes a fitting hole formed on a coupling surface of the holding body coupled to the cover, the projection fitted to the fitting hole, and a hole smaller in diameter than the fitting hole is formed on a bottom surface of the fitting hole.

* * * * *